US00RE35419E

United States Patent [19]

Kilty et al.

[11] E Patent Number: Re. 35,419

[45] Reissued Date of Patent: Jan. 7, 1997

[54] MEASUREMENT OF AN ENZYME MARKER AS AN AID TO DIAGNOSIS OF LIVER TRANSPLANT REJECTION

[75] Inventors: Cormac G. Kilty, 31 Monkstown Avenue, Monkstown, County Dublin; Seamus O'Byrne, 16 The Alders, Monkstown, Valley Monkstown, County Dublin, both of Ireland

[73] Assignees: Cormac G. Kilty; Seamus O'Byrne, both of County Dublin, Ireland

[21] Appl. No.: 134,026

[22] Filed: Oct. 5, 1993

Related U.S. Patent Documents

Reissue of:

[64] Patent No.: 5,217,868
Issued: Jun. 8, 1993
Appl. No.: 877,481
Filed: May 1, 1992

[51] Int. Cl.[6] ..... C12Q 1/48

[52] U.S. Cl. ..... 435/7.4; 435/7.94; 435/15

[58] Field of Search ..... 435/7.4, 7.94, 435/15

[56] References Cited

PUBLICATIONS

Calne, Liver Transplantation (2d Edition), 1987, pp. 301–303.
Hussey et al., Br. J. Anaesth., 60, 130–133 (1988).
Hayes et al., Clin. Chim. Acta, 172, 211–216 (1988).
Beckett et al., Clin. Chem., 35(6), 995–999 (1989).
Boss et al., Gastroenterology, 74(4), 859–594 (1978).
Sherman et al., Hepatology, 3(2), 162–169 (1983).
Haley et al., Biochem J., 254, 255–259 (1988).
Beckett et al., Clin. Chem., 35, 2186–2189 (1989).

*Primary Examiner*—David Saunders
*Attorney, Agent, or Firm*—Felfe & Lynch

[57] ABSTRACT

A method which assists in the early diagnosis of rejection in a liver transplant recipient comprises measuring an increase in plasma or serum alpha glutathione S-[tranferase]*transferase*(α-GST) from said recipient in the absence of or preceding any change in plasma or serum transaminase. α-GST is most suitably measured by enzyme-immunoassay, using a solid phase antibody which is monospecific for α-GST. The monospecific antibody cross-reacts with the α-GST dimers $B_1B_1$, $B_1B_2$ and $B_2B_2$.

7 Claims, 4 Drawing Sheets

MEASUREMENT OF AN ENZYME MARKER AS AN AID TO DIAGNOSIS OF LIVER TRANSPLANT REJECTION

Matter enclosed in heavy brackets [ ] appears in the original patent but forms no part of this reissue specification; matter printed in italics indicates the additions made by reissue.

FIELD OF THE INVENTION

This invention relates to a method which assists in the early diagnosis of rejection in a liver transplant recipient.

BACKGROUND AND PRIOR ART

In liver transplant recipients the risk of allograft rejection is greatest in the first few weeks after transplantation, although it can occur as late as the 8th post-operative month. Rejection is most common, however, between the 4th and 10th post-operative days. Prompt diagnosis is crucial to limit damage by this allogeneic immune response. It is also vital that the diagnosis is correct, since administration of augmented immunosuppression in the absence of rejection has its own morbidity—particularly in delaying wound healing and in predisposing the patient to serious infection. The most reliable evidence of rejection is histological but may not always be possible due to severe impairment of clotting. In current practice, the suspected diagnosis of rejection usually rests on evidence of progressive deterioration of liver function in the absence of any other explanation for this functional derangement (Calne, Ry, (1987); Liver Transplantation (2nd Edition), Ed Calne Ry, Grune & Stratton, Inc., London, 301–303). Thus, significant rejection is not diagnosed unless the serum bilirubin and alkaline phosphatase levels are elevated. If the serum transaminases and prothrombin time are also rising, then rejection is assumed unless there is evidence of(a) portal vein/hepatic artery obstruction, (b) septicaemia or (c) drug toxicity. The duration of treatment of rejection by augmented immunosuppression will depend on the improvement m liver function tests (LFTs). Patients with persistently raised LFTs have a poor prognosis.

The biochemical assessment of liver function usually includes measurement of plasma or serum aspartate aminotransferase (AST) or alanine aminotransferase (ALT) activity. These cytosolic enzymes are released into the circulation following hepatocellular damage. The measurement of these aminotransferases for monitoring liver function has been questioned, however, as activities may be normal in patients with chronic liver disease. The poor sensitivity of aminotransferases in detecting damage in certain types of liver pathology may partly lie in their distribution within the liver. The periportal hepatocytes contain the highest concentrations of the aminotransferases but the centrilobular hepatocytes, which are relatively deficient in aminotransferases, are more susceptible to damage from hypoxia and toxins such as alcohol and paracetamol.

Recently, the measurement of hepatic alpha glutathione S-transferase (α-GST) has been advocated as a superior marker of hepatocellular damage than the aminotransferases in a variety of clinical conditions including halothane hepatotoxicity (Hussey, A. J. et al. (1988): Br. J. Anaesth. 60, 130–135), autoimmune chronic active hepatitis (Hayes, P. C. et al. (1988); Clin. Chem. Acta., 172, 211–216), birth asphyxia (Beckett, G. J. et ai. (1989) Clin. Chem. 35, 995–999) and paracetamol poisoning (Beckett, G. J. et al. (1989); Clin. Chem., 35, 2186–2189). Indeed, studies of acute liver damage and chronic active hepatitis have indicated that GST activities, unlike those of transaminase, correlate better with histological abnormalities. (Bass, N. M. et al. (1978): Gastroenterology, 75, 589–594 and Sherman, M. et al. (1983): Hepatology, 3, 162–169).

The GSTs are a complex family of enzymes involved in detoxification. The enzymes catalyze the nucleophilic attack of glutathione (GSH) on a wide range of hydrophobic electrophiles. The GSTs can be divided into three classes: the basic, the near-neutral and the acidic enzymes according to their isoelectric points. These classes are related to the alpha (I), mu (II) and pi (III) families, respectively, in the rat (2). The human alpha class enzymes, also referred to as "ligandin" (3), comprise two subunits $B_1$ and $B_2$ which can hybridize to form the homodimers, $B_1B_1$ and $B_2B_2$ and the homodimer, $B_1B_2$ (4).

Adult liver contains perdominantly the basic or α-GST. One of the properties of hepatic GST which may partly explain its greater sensitivity as a marker of liver damage when compared with the aminotransferases is its wider distribution within the liver. Immunohistochemical studies of GST in human foetuses, neonates and adults have shown that the basic and acidic GST are equally expressed in both periportal and centrilobular hepatocytes (Hiley C. et al. (1988); Biochem. J., 284, 255–259). Other properties of GSTs also offer theoretical advantages over measurements of aminotransferases in the investigation of liver damage. They are relatively small enzymes (MW~50,000) and are present in high concentrations in the hepatocyte cytosol. GSTs are readily and rapidly released in quantity into the circulation following hepatic damage: their short plasma half-life (<90 min.) allowing early detection of hepatic damage and its resolution.

Histologically the acute rejection process appears to begin with a mononuclear cell infiltration of portal tracts. It is noteworthy that spillover of lymphocytes into the adjacent periportal parenchyma is occasionally but not always a feature of acute rejection. There may also be involvement of centrilobular blood vessels and bile ducts. The pattern of infiltration within the liver is also variable—ranging from focal to diffuse. The diagnostic sensitivity of the transaminases as early markers of rejection depends on their distribution within the liver in relation to those sites involved at the beginning of the rejection process. If the periportal hepatocytes are not affected in this early pathological process, changes in transaminases may not always be expected to rise markedly and diagnosis and treatment could be delayed. This may be particularly important in the first few days after transplantation, when the patient is at greatest risk of rejection and transaminases remain elevated as a result of ischaemia and surgical trauma to the liver.

It is an object of the present invention to provide a method which assists in the early diagnosis of rejection in liver transplant recipients.

It is a further object of the present invention to provide a more sensitive and specific marker of the rejection process in the liver transplant recipient than has heretofore been available.

It is a still further object of the present invention to provide a method for the monitoring of post-operative liver transplant patients so that earlier corrective action can be taken which may prevent rejection occurring.

SUMMARY OF THE INVENTION

A method which assists in the early diagnosis of rejection in a liver transplant recipient, which comprises measuring an increase in plasma or serum alpha glutathione S-transferase (α-GST) from said recipient in the absence of or preceding any change in plasma or serum transaminase and an antibody which is monospecific for α-GST.

Figure 1:
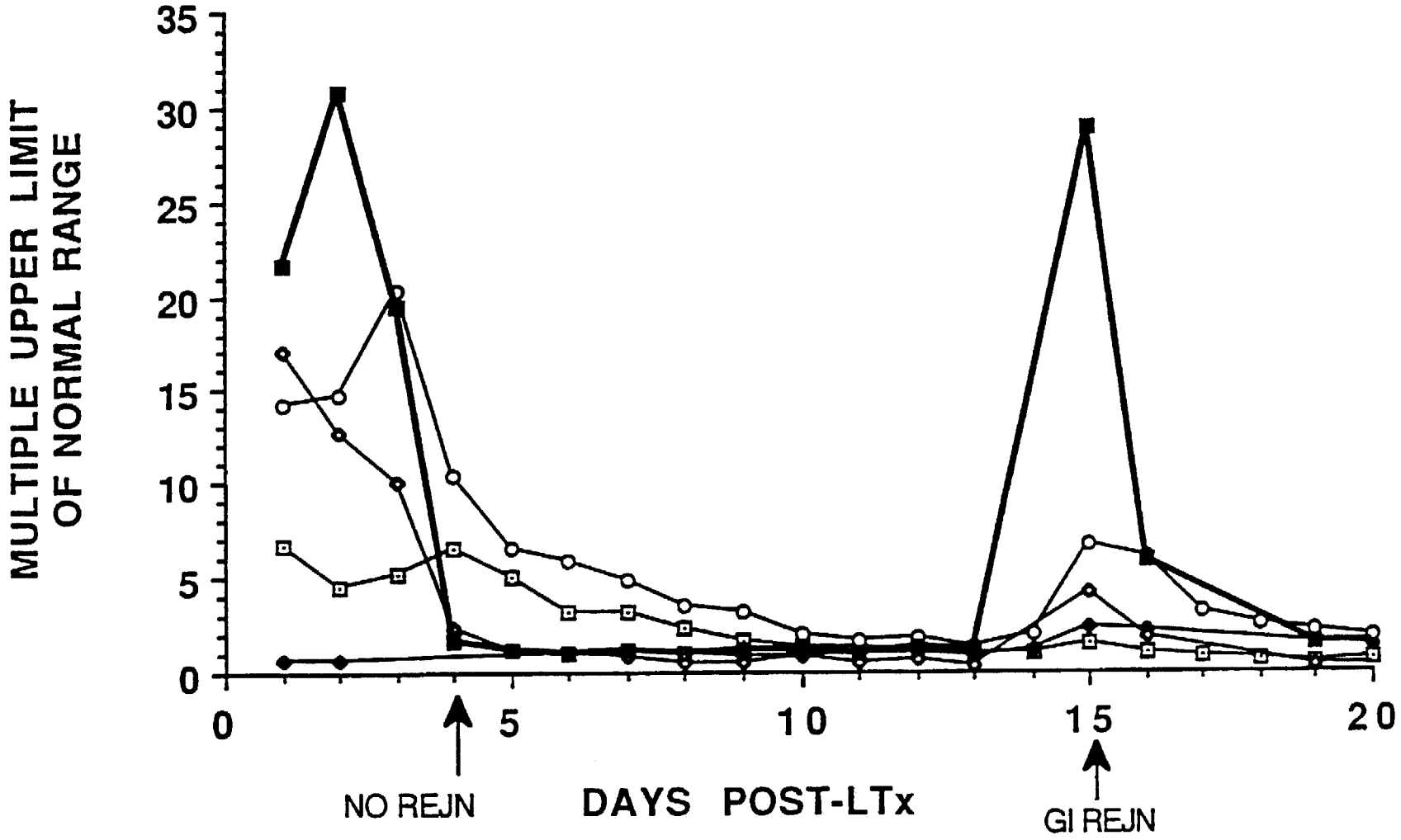
FIG. 1 is a graph of multiple upper limit of normal range for a number of markers, including α-GST, versus day post liver transplant for a first recipient.
Figure 2:
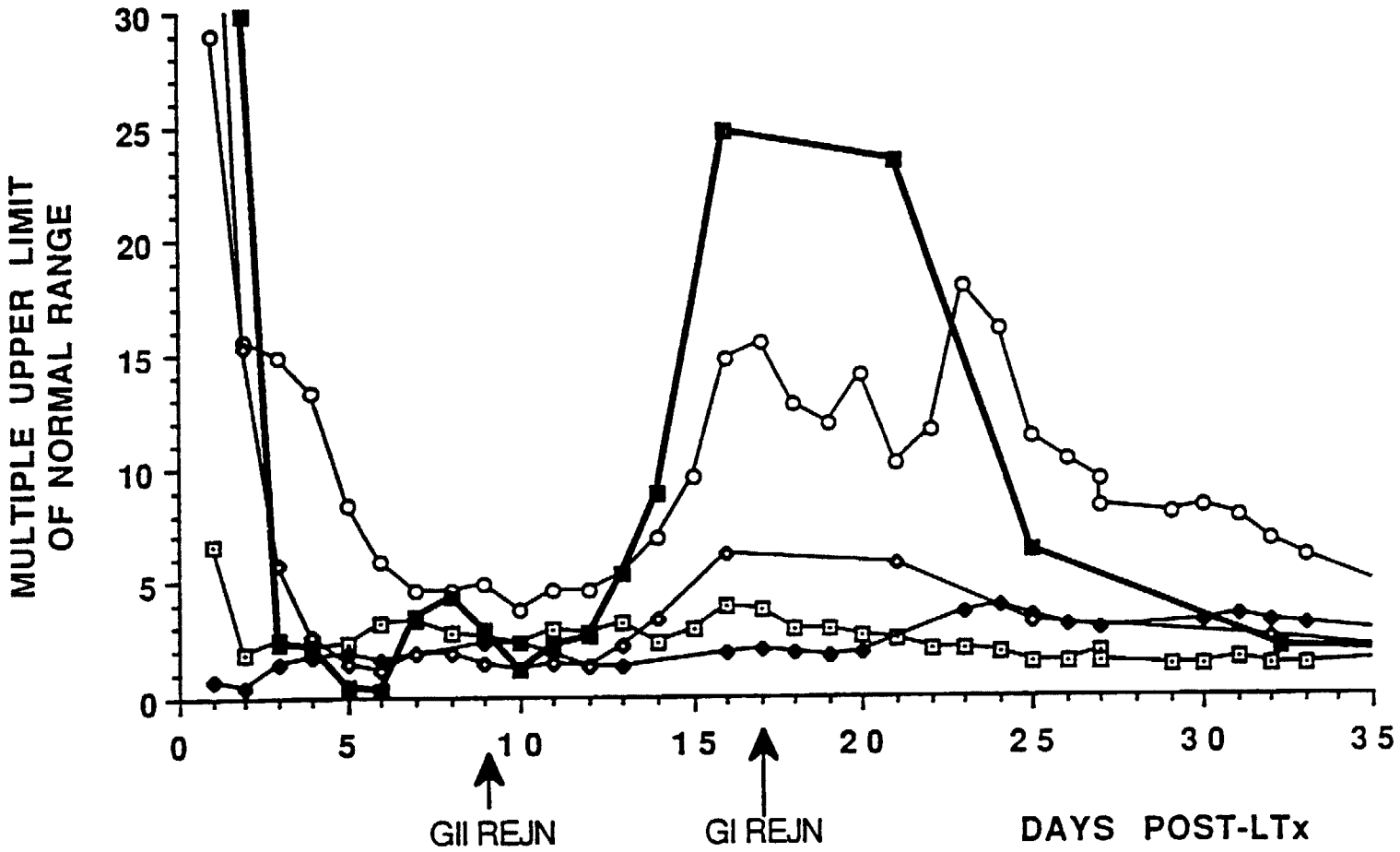
FIG. 2 is a graph of multiple upper limit of normal range for a number of markers, including α-GST, versus day post liver transplant for a second recipient.
Figure 3:
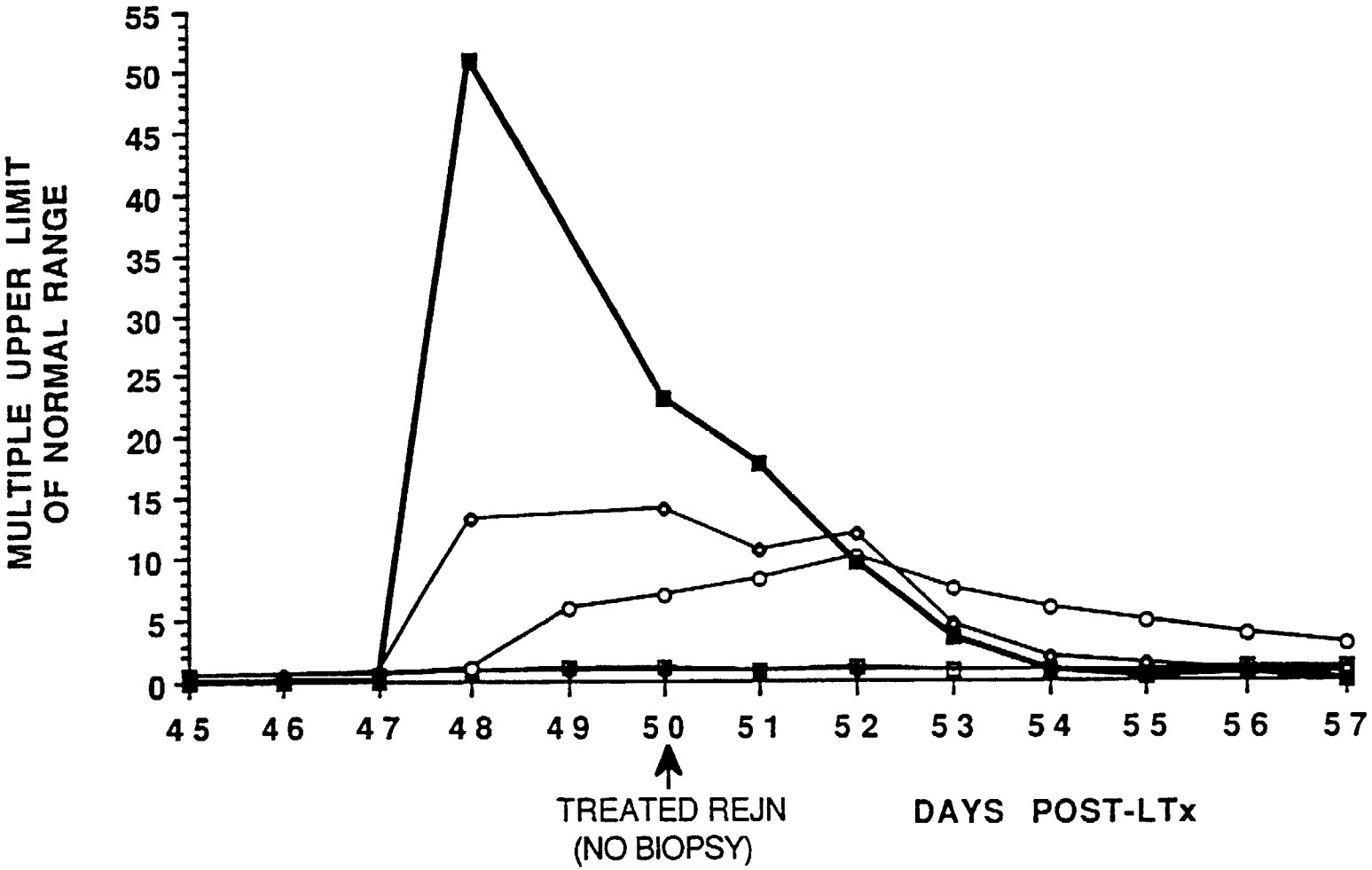
FIG. 3 is a graph of multiple upper limit of normal range for a number of markers, including α-GST, versus day post liver transplant for a third recipient.
Figure 4:
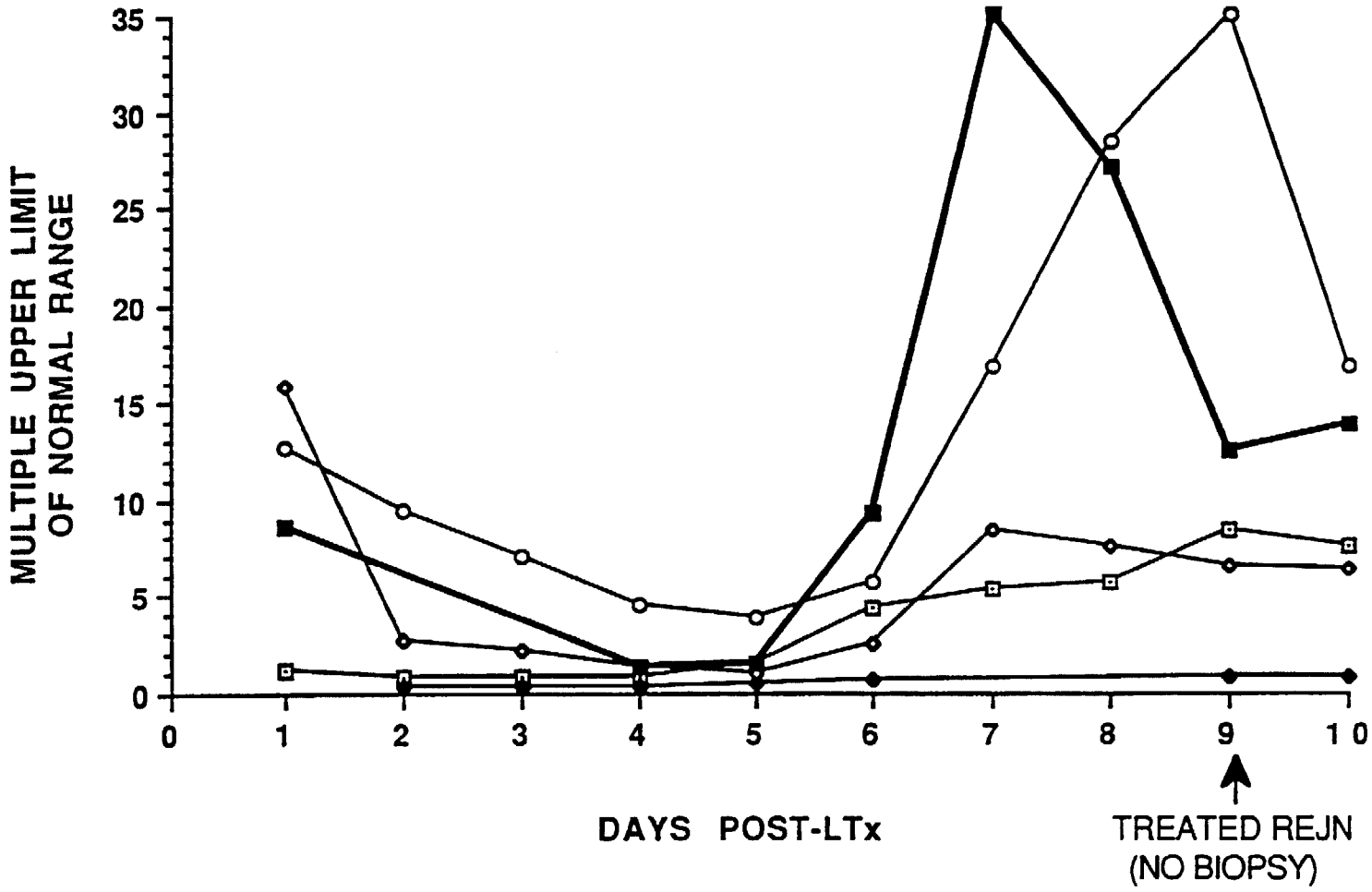
FIG. 4 is a graph of multiple upper limit of normal range for a number of markers, including α-GST, versus day post liver transplant for a fourth recipient.

In each of FIGS. 1–4, [-■-■-] -▣-▣-represents bilirubin (BILI), -◆-◆-represents alkaline phosphatase [(ALT)] *ALP*, ○○ represents ALT, [-●-●-] -◆-◆-represents AST and [-▣-▣-] -■-■-represents α-GST.

DETAILED DESCRIPTION OF PREFERRED EMBODIMENTS

In the method according to the invention, the α-GST is preferably measured by enzymeimmunoassay.

In a particularly preferred embodiment of the invention there is used as solid phase an antibody which is monospecific for α-GST, more especially a monospecific antibody which cross-reacts with the α-GST dimers $B_1B_1$, $B_1B_2$ and $B_2B_2$.

Further, preferably, the antibody for use in accordance with the invention does not cross-react with either GST-mu or GST-pi.

The enzymeimmunoassay for use in accordance with the invention is preferably one that can quantify the level of α-GST in human plasma or serum to a sensitivity limit of 0.75 ng/ml.

Also in accordance with the invention, the enzymeimmunoassay enables one to measure an increase in α-GST within a time period of less than five hours, more especially less than four hours.

The invention also provides a polyclonal antibody for use in a method according to the invention as hereinbefore defined and which cross-reacts with the α-GST dimers $B_1B_1$, $B_1B_2$ and $B_2B_2$.

It will be appreciated that a monoclonal antibody having the requisite specificity can also be used in the method according to the invention.

Such a monoclonal antibody may suitably be human, mouse or rat monoclonal antibody prepared by conventional methods, including those methods currently available for producing monoclonal antibody on a commercial scale, genetically engineered monoclonal antibody or antibody fragments or antibody produced by in vitro immunisation of suitable cells.

An enzymeimmunoassay in accordance with the invention can be carried out using any known format, such as, for example beads, dip-sticks, membranes, particles, plates, rods, strips, tubes or wells.

For example, insolubilised or solid phase antibody as used herein is suitably bound to a bead, dip-stick, membrane, particle, plate, rod, strip, tube or well of plastics material or glass in a manner known per se. More specifically, the insolubilised form of the antibody comprises said antibody adsorbed on a surface adapted for protein adsorption such as a bead, dip-stick, membrane, particle, plate, rod, strip, tube or well.

In an especially preferred embodiment, the surface comprises a plastics microtitration plate or strip adapted for protein adsorption wherein the immunochemical reaction and the estimation of α-GST can take place. Especially suitable microtitration plates are gamma-irradiated microtitration plates. Examples of such gamma-irradiated microtitration plates are flat-well polystyrene microtitration plates marketed by DYNATECH under the Trade Mark MICROELISA and those sold under the Trade Mark "NUNC" IMMULON. Examples of strips are strips marketed by DYNATECH under the Trade Mark REMOVAWELL.

The relevant surface may be coated directly with an optimum dilution of polyclonal antibody prepared by separating the relevant immunoglobulin fraction of antiserum.

The estimation of the bound α-GST is preferably carried out by enzymeimmunoasay using an enzyme-label. The labelled enzyme can be prepared in conventional manner or purchased from appropriate suppliers. A suitable enzyme label is an enzyme conjugate comprising an enzyme-labelled antibody for use in a competitive binding assay. The estimation of the bound α-GST is preferably carried out by enzymeimmunoassay using a suitable peroxidase labelled antibody or other suitable peroxidase conjugate. A suitable peroxidase is horse radish peroxidase. One such other suitable peroxidase conjugate is an avidin-biotin peroxidase complex, which can be used with an antibody biotin conjugate to amplify the enzyme assay in conventional manner. In such an enzyme assay antigen insolubilised on solid phase antibody binds to the antibody-biotin complex which in turn binds to the avidin/streptavidinbiotin peroxidase complex, whereupon the peroxidase activity is measured.

The estimation of the bound α-GST can also be carried out by fluorometric, luminometric or radiometric assay, using fluorochromes, light-emitting probes or radio labels, respectively.

The invention will be further illustrated by the following Examples.

EXAMPLE 1

Polyclonal antibody production

1) Antigen purification

Approximately 1 g of human liver was homogenised in 3 volumes of a homogenising buffer at pH 7.2 having the following composition:

0.25M sucrose
10 mM Tris/HCl
1 mM EDTA in a Waring Blender for 3 min. The homogenate was centrifuged at 16,000 g for 20 min. and the supernatant decanted and centrifuged at 45,000 g for 1 h. The resulting supernatant was decanted and the retentate filtered through glass wool, followed by dialysis against 20 liters 10 mM Tris, pH 7.8, 0.2M NaCl (buffer 1) overnight at 4° C. The dialysate was centhfuged at 16,000 g for 10 min. The supernatant was then applied to an S-hexylGSHagarose column equilibrated in buffer 1 and washed with buffer 1 until $E_{280}=0$.

The column was eluted with 0.03 mM S-hexylGSH in buffer 1.

The protein peaks (a-GST-basic pool) was pooled and the pooled material dialysed against 2×5 liters 10 mM sodium phosphate buffer at pH 7.0. The dialysate was checked by SDS PAGE, isoelectric focussing (urea) and enzyme activity in hydrolysing chloro-2,4-dinitrobenzene (cDNB).

Yield~30 mg protein.

The α-GST was stored in aliquots at −20° C. until required for use.

2) Antisera production

Day 1.

200 μg of α-GST obtained in step 1 in 0.5 ml buffer 1 and 0.5 ml Freund's complete adjuvant was vortexed for 2 h. to form an emulsion. The antigen emulsion was [infection]*injected* intradermally into multiple sites on to the previously shaved back of a rabbit.

Day 21

The procedure at day 1 was repeated except that the antigen emulsion was injected intramuscularly into the leg of the rabbit.

Day 31

The procedure for day 21 was repeated.

Day 38

Blood samples were collected from an ear vein. The serum collected and [IgC]*IgG* polysera purified on protein A-agarose.

A stock anti-α-GST IgG was prepared containing 2.98 mg/ml.

EXAMPLE 2

Enzymeimmunoassay

Plasma samples are dispensed (200 μl) into duplicate microtitre wells coated with purified monospecific antibody to α-GST (1 μg/well in 0.1M carbonate/bicarbonate buffer, pH 9.6) as prepared in Example 1 and into a number of positive control wells containing a preparation of purified α-GST from human liver (50 ng/ml). The positive controls are diluted with phosphate buffered saline containing TWEEN 20 (25%) (TWEEN is a Trade Mark) (PBST). The positive control panel for the standard curve is prepared as follows:

| | | | | | | |
|---|---|---|---|---|---|---|
| Final concentration (ng/ml): | 25 | 10 | 5 | 2.5 | 0.75 | 0 |
| Positive Control (μl): | 250 | 100 | 50 | 25 | 7.5 | 0 |
| PBST (μl) | 250 | 400 | 450 | 475 | 492.5 | 500 |

High level plasma samples can be diluted with PBST to bring them onto a linear scale. All wells are then incubated at room temperature for 1 hour.

The sample is then removed and the wells are washed with PBST four times.

A working dilution of biotinylated anti-GST is prepared by diluting 1/400 concentrated biotinylated anti α-GST (1.7 mg/ml) with PBST. 50 μl of the latter is dispensed into each well and the wells are incubated at room temperature for 1 hour.

The solution is removed and the wells are washed with PBST four times.

A working dilution of streptavidin biotinylated peroxidase complex is prepared to give a concentration of 0.4/μg/ml with peroxidase activity of 0.08 units/ml and 50 μl of the latter is dispensed into each well. The wells are again incubated at room temperature for one hour. The latter solution is removed and the wells are washed six times with PBST. Tetramethyl benzdine (TMB) chromogen containing 0.03% hydrogen peroxide in 0.1M citrate/carbonate buffer, pH 5.0 is added to each well (200 μl). The colour is allowed to develop for 15 min. and then the reaction is stopped by adding $2NH_2SO_4$ (50 μl). The wells are read at 450 nm. The mean results are calculated, the standard curve is graphed and unknown sample values obtained by extrapolation in conventional manner.

An o-phenylene diamine (OPD) chromogen can also be used.

EXAMPLE 3

Preliminary retrospective study

A retrospective, longitudinal study of liver function in 11 consecutive adult liver transplant recipients, in the period up to 3 months after transplantation has been carried out on our behalf at Addenbrook's Hospital, Cambridge, U.K. by Dr. Andrew Trull. All samples sent for routine LFTs, including serum billrubin (BILI), alkaline phosphatase (ALP) and ALT were also assayed for serum AST and α-GST. Longitudinal results were plotted as a multiple of the upper limit of the normal range (ULN) for each analyte to bring covariate data onto a comparable scale. Each patient's clinical course was carefully reviewed with particular attention being paid to the documentation of events that might influence liver function. These included rejection, vascular/biliary obstruction, infection, surgical/invasive procedures such as laparotomy or biopsy and the demonstration of potentially hepatotoxic drugs. The diagnosis of rejection was usually based upon histopathology but in those cases where a biopsy was not carried out, despite clinical evidence of rejection, treatment with augmented immunosuppression was considered diagnostic. In this study the ULN values for the markers measured were as follows:

| | |
|---|---|
| BILI | 17 μmoles/liter |
| ALP | 135 units/liter |
| ALT | 40 units/liter |
| AST | 37 units/liter |
| α-GST | 10 μg/liter |

Longitudinal LFT results from four of the liver transplant recipients studied are shown in FIGS. 1–4.

Case 1 (FIG. 1) illustrated the importance of the short half-life of α-GST. High levels of GSTs following transplantation fell rapidly from nearly 35 times the ULN to only 3 times the ULN by the high risk period at day 4. A biopsy taken on day 4 showed no evidence of rejection and α-GST concentrations continued to fall, consistent with this finding. On day 4 the ALT activity was still 10 times the ULN falling only slowly after transplantation. Good baseline levels of all LFTs were seen until day 15 when Grade 1 rejection was diagnosed histologically. The 3 to 5-fold increases in transaminases at this time compare with a 30-fold increase in α-GST, illustrating the greater sensitivity of serum α-GST measurements in the rejection process.

Case 2 (FIG. 2) further illustrates the importance of the short half-life of α-GST in the early post-operative period. The first rejection episode in this patient, diagnosed by biopsy on day 9, was marked by a 6-fold increase in α-GST but no comparable rise in other LFTs was found. The changes in α-GST seen preceding the second biopsy-proven rejection episode on day 17 are also important because marked changes in α-GSTs were apparent at least 2 days earlier than changes in transaminases.

Case 3 (FIG. 3) illustrates the dramatic changes in α-GST seen in some patients in the absence or preceding any change in transamtnases during rejection. Here the peak in α-GST preceded the ALT peak by 4 days, yet α-GST levels had returned to normal more than 3 days before the ALT.

Case 4 (FIG. 4) also shows the earlier greater and more defined changes in α-GST in a patient treated for rejection (without biopsy confirmation) on day 9.

Although a full clinical review of all 11 cases is still underway overall GST appears to be a more sensitive and specific marker of the early rejection process. Its potential clinical value, predicted from its physico-chemical properties, has been substantiated by this longitudinal, retrospective study, α-GST, as an adjunct to clinical indices of rejection, may prove to be sufficiently specific for rejection to avoid the requirement for biopsy which has its own morbidity and mortality. It is postulated that the method according to the invention has the potential to improve the management of transplant patients with possible reduction in hospital time. It may also improve the assessment, of the various medication regimes that a patient must receive particularly allowing the physician to cease administration of potentially damaging treatments at an earlier stage.

Thus the expected clinical advantages of the method according to the invention for measurement of hepatic α-GST in liver transplant recipients over conventional LFTS can be summarised as follows:

(a) the short half-life of α-GST may be expected to result in a more rapid fall to normal baseline concentrations following surgically uncomplicated transplantation; potentially improving the resolution of subsequent changes in liver function;

(b) the development of different patterns of rejection are more likely to be revealed early and more consistently by the relatively large changes in α-GST due to the enzyme's high cytosolic concentration in hepatocytes and more general distribution throughout the liver; and (c) it should be possible to monitor the resolution of rejection following treatment more closely—again due to the short half-life of α-GST in the circulation. Thus, it may be possible to stop administration of augmented immunosuppression earlier.

The invention is not limited to the embodiments described above, which may be modified and/or varied without departing from the scope of the invention.

What we claim is:

1. Method for assisting in early diagnosis of liver transplant rejection, comprising measuring the level of alpha glutathione S transferase in a plasma or serum sample of a liver transplant patient, and comparing said level to a normal level, wherein an increase in said alpha glutathione S transferase level in said liver transplant patient in the absence of or preceding any change in plasma transaminase level or serum transaminase level is indicative of liver transplant rejection.

2. Method of claim 1, comprising measuring said alpha glutathione S-transferase via an enzyme immunoassay.

3. Method of claim 2, wherein said enzyme immunoassay further comprises contacting said sample with a solid phase bound, alpha glutathione S-transferase specific antibody.

4. Method of claim 3, wherein said antibody [is not] cross reacts with alpha glutathione S transferase dimers $B_1B_1$, $B_1B_2$, and $B_2B_2$.

5. Method of claim 3, wherein said antibody is not cross reactive with either of glutathione S transferase-mu or glutathione S transferase-pi.

6. Method of claim 2, comprising measuring said alpha glutathione S transferase to a limit of 0.75 ng/ml.

7. Method of claim 2, wherein said enzyme immunoassay is carried out in less than 5 hours.

* * * * *